United States Patent
Lee et al.

(10) Patent No.: US 12,426,807 B2
(45) Date of Patent: Sep. 30, 2025

(54) APPARATUS AND METHOD FOR EVALUATING FORCE CONTROL ABILITY OF UPPER LIMB AND PROSTHESIS

(71) Applicant: KOREA INSTITUTE OF SCIENCE AND TECHNOLOGY, Seoul (KR)

(72) Inventors: Song Joo Lee, Seoul (KR); Sang Rok Oh, Seoul (KR); Sangsoo Park, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 368 days.

(21) Appl. No.: 17/020,809

(22) Filed: Sep. 15, 2020

(65) Prior Publication Data

US 2021/0244320 A1     Aug. 12, 2021

(30) Foreign Application Priority Data

Feb. 11, 2020  (KR) ........................ 10-2020-0016266

(51) Int. Cl.
*A61B 5/11*     (2006.01)
*A61B 5/00*     (2006.01)
*A61B 5/22*     (2006.01)

(52) U.S. Cl.
CPC ............ *A61B 5/1124* (2013.01); *A61B 5/224* (2013.01); *A61B 5/4851* (2013.01); *A61B 5/72* (2013.01); *A61B 5/742* (2013.01); *A61B 2505/09* (2013.01); *A61B 2560/0487* (2013.01)

(58) Field of Classification Search
CPC ..... A61B 5/1124; A61B 5/224; A61B 5/4851; A61B 5/72; A61B 5/742; A61B 2505/09; A61B 2560/0487
See application file for complete search history.

(56) References Cited

U.S. PATENT DOCUMENTS

| 5,830,160 A | * | 11/1998 | Reinkensmeyer ..... A61B 5/224 600/595 |
| 6,413,229 B1 | | 7/2002 | Kramer et al. |

(Continued)

FOREIGN PATENT DOCUMENTS

| JP | 2002-95710 A | 4/2002 |
| JP | 2004-41519 A | 2/2004 |

(Continued)

OTHER PUBLICATIONS

Machine Translation of JP-5154558-B2, Patent Translate, pp. 1-30, printed on Nov. 7, 2022 (Year: 2013).*

(Continued)

*Primary Examiner* — Jennifer Robertson
*Assistant Examiner* — Om Patel
(74) *Attorney, Agent, or Firm* — CANTOR COLBURN LLP

(57) ABSTRACT

The apparatus for evaluating force control ability according to an embodiment includes: a display unit configured to display a target force direction; a measuring unit configured to measure a direction and magnitude of a force applied by a user; and a processing unit configured to evaluate force control ability of the user by comparing the measured force direction with the target force direction and comparing the measured force magnitude with a predetermined reference force magnitude.

2 Claims, 3 Drawing Sheets

(56) References Cited

U.S. PATENT DOCUMENTS

| | | | | |
|---|---|---|---|---|
| 7,503,878 | B1* | 3/2009 | Amsbury | A61B 5/1122 |
| | | | | 482/3 |
| 2008/0221487 | A1* | 9/2008 | Zohar | A61B 5/1127 |
| | | | | 600/595 |
| 2017/0354367 | A1* | 12/2017 | Laghi | A61F 2/80 |
| 2018/0085016 | A1 | 3/2018 | Kang et al. | |

FOREIGN PATENT DOCUMENTS

| | | | | |
|---|---|---|---|---|
| JP | 2005-348779 | A | 12/2005 | |
| JP | 4351808 | B2 * | 10/2009 | A61B 5/1036 |
| JP | 5154558 | B2 * | 2/2013 | A61B 5/0488 |
| JP | 2018-171523 | A | 11/2018 | |
| KR | 1020030089019 | A | 11/2003 | |
| KR | 101541095 | B1 | 8/2015 | |
| KR | 20160013847 | * | 2/2016 | |
| KR | 10-2016-0141095 | A | 12/2016 | |
| KR | 20160141095 | * | 12/2016 | |
| KR | 10-2017-0135459 | A | 12/2017 | |
| SG | 10201902350 | A1 * | 4/2019 | A61B 17/74 |
| TW | 200942221 | * | 10/2009 | |
| WO | WO-2005074370 | A2 * | 8/2005 | A61B 34/30 |
| WO | WO-2006054490 | A1 * | 5/2006 | A61B 5/1072 |
| WO | WO-2006069264 | A1 * | 6/2006 | A61B 5/112 |
| WO | WO-2014159577 | A1 * | 10/2014 | A61B 5/1124 |
| WO | WO-2015038979 | A1 * | 3/2015 | A61B 17/154 |

OTHER PUBLICATIONS

Machine Translation of KR-20160141095, Patent Translate, pp. 1-10, printed on Nov. 7, 2022 (Year: 2016).*

Machine Translation of TW-200942221, Patent Translate, pp. 1-10, printed on Nov. 7, 2022 (Year: 2009).*

Machine Translation of WO-2006054490, Patent Translate, pp. 1-27, printed on Nov. 8, 2022 (Year: 2006).*

Machine Translation of JP-4351808-B2, Patent Translate, pp. 1-31, printed on Oct. 13, 2023 (Year: 2009).*

Machine Translation of KR 20160013847, Patent Translate, pp. 1-38, printed on May 16, 2024 (Year: 2016).*

* cited by examiner

APPARATUS AND METHOD FOR EVALUATING FORCE CONTROL ABILITY OF UPPER LIMB AND PROSTHESIS

DESCRIPTION OF GOVERNMENT-FUNDED RESEARCH AND DEVELOPMENT

This research has been conducted with the support of the Korea Research Foundation (Bionic Arm Mechatronics Convergence Technology Development Project, Project Serial No.: 2014M3C1B2048419) under the supervision of the Korea Institute of Science and Technology and funded by the Ministry of Science and ICT.

CROSS-REFERENCE TO RELATED APPLICATION

This application claims priority to Korean Patent Application No. 10-2020-0016266, filed on Feb. 11, 2020, and all the benefits accruing therefrom under 35 U.S.C. § 119, the contents of which in its entirety are herein incorporated by reference.

BACKGROUND

1. Field

The present disclosure relates to an apparatus and method for evaluating force control ability of an upper limb or prosthesis, and more particularly, to an apparatus and method configured to evaluate force control ability by comparing a direction and magnitude of a force applied by upper limb (hand, arm, shoulder) muscles of a user or through a prosthesis that the user wears with a target force direction and a reference force magnitude.

2. Description of the Related Art

Rehabilitation training is a program that is provided to recover body functions when a motor function of the body part is deteriorated due to an injury. In general, the emphasis is placed on improving muscle strength and restoring muscle nerves by repeatedly moving parts of the body whose function is degraded according to the instructions of a medical staff or rehabilitation trainer.

Recently, technology to assist the rehabilitation training through computer devices and programs has been developed. For example, if a computer device other than a medical staff delivers instruction to a patient through a display, the patient performs a physical motion according to the instruction, and the computer device detects the physical motion through a sensor to determine whether the patient has performed the motion correctly. The computer may assist in rehabilitation training of the patient by providing a corresponding feedback to the patient or medical staff.

Conventional rehabilitation training assisting devices and programs are mainly focused on evaluating the performance of a patient according to the movement in daily life in a time measurement method. For example, a patient with an injured right arm is instructed to move an object from a point A to a point B using the right hand, and the body control ability of the patient is evaluated by measuring the time required to perform the motion. According to another prior art, in the above example, a sensor may be attached to the right arm of the patient to measure the angle of a joint or obtain additional information such as an electromyogram (EMG) signal to evaluate a specific weakness of the body part.

However, according to the conventional rehabilitation training method, the ability to perform a specific motion may be evaluated just by measuring an amount of time required to perform the motion, and it is not possible to provide specific information about the magnitude of a force required for the patient to interact with an object using the body or whether the force is applied in a proper direction. Therefore, it is difficult to quantitatively evaluate the force control ability of a patient by the conventional method, and it is difficult to objectively grasp a weak part of the body part.

SUMMARY

The present disclosure is designed to solve the above problems, and the present disclosure is directed to providing an apparatus, which evaluates force control ability by measuring a direction and magnitude of a force applied by a user to a measurement tool and comparing the direction and magnitude with a target force direction and a reference force magnitude, in order to evaluate the force control ability required for the user to directly interact with an object.

The present disclosure is also directed to providing an apparatus, which evaluates a force control ability of a prosthesis by measuring a direction and magnitude of a force applied to a measurement tool using the prosthesis worn by the user and comparing the direction and magnitude with a target force direction and a reference force magnitude.

In one aspect, there is provided an apparatus for evaluating force control ability, comprising: a display unit configured to display a target force direction; a measuring unit configured to measure a direction and magnitude of a force applied by a user; and a processing unit configured to evaluate force control ability of the user by comparing the measured force direction with the target force direction and comparing the measured force magnitude with a predetermined reference force magnitude.

According to an embodiment, the processing unit may be configured to evaluate force control ability of the user by extracting a component of the force applied in the same direction as the target force direction among components of the measured force and comparing a magnitude of the extracted force with the predetermined reference force magnitude.

According to an embodiment, the apparatus for evaluating force control ability may be configured to evaluate force control ability of an upper limb of the user by measuring a direction and magnitude of the force applied by the upper limb of the user.

According to an embodiment, the measuring unit may be configured to receive information about the direction and magnitude of the force from a force measurement tool configured such that the user applies a force while gripping the force measurement tool.

According to an embodiment, the processing unit may be configured to display feedback information according to the evaluation of the force control ability of the user through the display unit.

According to an embodiment, the feedback information may include diagnosis information about a body part of the user with weak force control ability.

According to an embodiment, the apparatus for evaluating force control ability may further comprise a fixing unit configured to fix a portion of the body of the user so that a force by body parts other than the body part subject to force control ability evaluation does not intervene.

In another aspect of the present disclosure, there is also provided an apparatus for evaluating force control ability of a prosthesis, comprising: a display unit configured to display a target force direction; a measuring unit configured to measure a direction and magnitude of a force applied by a user through a prosthesis; and a processing unit configured to evaluate force control ability of the prosthesis by comparing the measured force direction with the target force direction and comparing the measured force magnitude with a predetermined reference force magnitude.

In another aspect of the present disclosure, there is also provided a method for evaluating force control ability, which is performed by a computer processor, the method comprising: displaying a target force direction on a display; measuring a direction and magnitude of a force applied by a user; extracting a component of the force applied in the same direction as the target force direction among components of the measured force; and evaluating force control ability of the user by comparing a magnitude of the extracted force with the predetermined reference force magnitude.

In another aspect of the present disclosure, there is also provided a computer program for performing the method for evaluating force control ability according to an embodiment, the computer program being stored in a computer-readable recording medium.

If the apparatus for evaluating force control ability according to an embodiment of the present disclosure is used, unlike the prior art where the control ability of a user is evaluated simply according to the time taken to perform a motion, it is possible to evaluate the force control ability required to interact directly with an object by using an upper limb (hand, arm, shoulder, or the like) of the user. According to the embodiment, it is possible to quantitatively evaluate the force control ability of a body part interacting with the object while minimizing the intervention of other body parts that are not injured. According to the quantitative evaluation method, a body part with weak force control ability may be diagnosed objectively, thereby improving the efficiency of rehabilitation training.

According to another embodiment of the present disclosure, it is possible to quantitatively evaluate the force control ability of a prosthesis by measuring a direction and magnitude of a force applied to a measurement tool in a state where the user wears the prosthesis and comparing the direction and magnitude with a target force direction and a reference force magnitude.

DETAILED DESCRIPTION

The terms used in this specification are selected as general terms that are widely used as possible at the present in consideration of functions but may vary according to the intention or custom of those skilled in the art or the emergence of new technologies. In addition, in certain cases, a term may be arbitrarily selected by the applicant, and in this case, the meaning of the term will be described in the corresponding specification. Therefore, it should be noted that the term used in this specification should be interpreted based on the actual meaning of the term and the entire contents of this specification, rather than a simple name of the term.

In addition, embodiments described in this specification may be entirely hardware, partially hardware and partially software, or entirely software. In this specification, "unit", "device" or "system" refers to a computer-related entity such as hardware, a combination of hardware and software, or software. For example, "unit", "device" or "system" may refer to hardware constituting a part or all of a platform and/or software such as an application for operating the hardware.

Hereinafter, embodiments will be described in detail with reference to the accompanying drawings and contents illustrated in the accompanying drawings, but the scope to be claimed is not limited or restricted by the embodiments.

Figure 1:
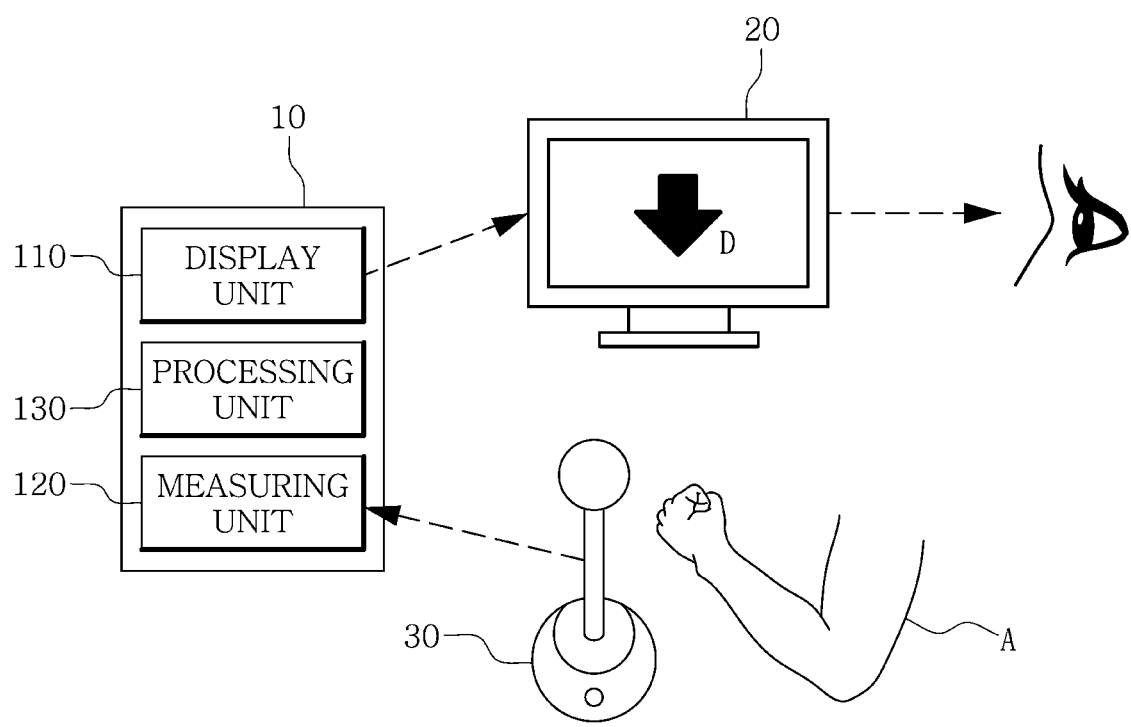
FIG. 1 is a diagram for illustrating the configuration and operation of an apparatus for evaluating force control ability according to an embodiment.

FIG. 1 is a diagram for illustrating the configuration and operation of an apparatus for evaluating force control ability according to an embodiment. Referring to FIG. 1, the apparatus 10 for evaluating force control ability according to an embodiment may include a display unit 110, a measuring unit 120, and a processing unit 130.

The display unit 110 is a component for displaying a target force direction to a user. In this specification, the user is a person who wants to evaluate force control ability of a body part through the apparatus and may correspond to a patient who needs rehabilitation training due to a deteriorated function caused by an injury or an athlete who wants to receive a quantitative evaluation of physical ability. The target force direction refers to a direction that is a standard for evaluating force control ability of the user, namely a specific direction in which the user applies a force using a body part according to an instruction.

In an embodiment, the display unit 110 sequentially outputs images indicating the target force direction on a display according to an evaluation program by using a displaying device such as a display. Referring to FIG. 1, the display unit 110 instructs the user to apply a force in the target force direction, namely in a downward direction, by outputting an image D in the form of an arrow pointing the downward direction on the display 20. The image D shown in FIG. 1 is an example, and various types of images indicating a specific direction may be used.

According to an embodiment, the display 20 may be a display device worn on the head like a head-mounted display (HMD) and outputting an image indicating the target force direction. According to another embodiment, the display unit 110 may be configured to output a voice that presents the target force direction rather than an image by using a voice output device (not shown) such as a speaker. For example, the speaker may present the target force direction to the user by outputting an instruction voice such as "Apply a force downward".

The measuring unit 120 is a component to measure the direction and magnitude of a force applied by the user. Referring to FIG. 1, if the user applies a certain amount of force to a force measurement tool 30 according to the target force direction displayed on the display 20, the measuring unit 120 measures the direction and magnitude of the force applied by the user to the force measurement tool 30 in real-time and store the measurement data in a storage device such as a memory.

According to an embodiment, the apparatus 10 for evaluating force control ability is configured to evaluate the force control ability of an upper part (more specifically, hand, arm, shoulder) of the user. For this, the force measurement tool 30 may be used such that the user may apply a force while gripping the force measurement tool 30. As shown in FIG. 1, the force measurement tool 30 according to an embodiment may be manufactured in a form in which the user may hold the force measurement tool 30 in his hand and move in various directions (for example, a rod-type vertically standing on the floor). A sensor (for example, a 6-axis sensor) capable of detecting changes of an inclination direction, speed, and torque of the bar may be included in the force measurement tool 30. The information detected by the sensor, namely information related to the direction and magnitude of the force, is transmitted to the measuring unit 120 in the form of an electrical signal, and the measuring unit 120 measures the direction and magnitude of the force applied at the present to the measuring tool based on the input signal.

The processing unit 130 is a component for evaluating force control ability of the user by comparing the measured force direction measured by the measuring unit 120 with the target force direction and comparing the measured force magnitude with a predetermined reference force magnitude. The force control ability refers to the ability to apply a force with a desired intensity in a desired direction by a body part of the user. That is, the processing unit 130 determines whether the user may control the force of a desired direction and magnitude by comparing the direction and magnitude of the force obtained as data by the force measurement tool 30 and the measuring unit 120 with the reference direction and magnitude.

According to an embodiment, the processing unit 130 may be configured to evaluate control ability of the user by extracting a component of the force applied in the same direction as the target force direction among components of the measured force and comparing the magnitude of the extracted force with the predetermined reference force magnitude.

Figure 2:
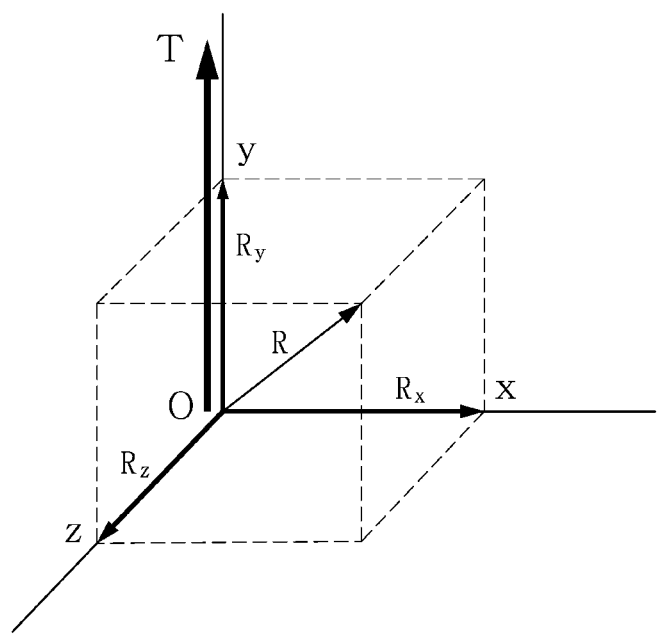
FIG. 2 is a diagram for illustrating a method for analyzing components of a measured force by the apparatus for evaluating force control ability according to an embodiment.

FIG. 2 is a diagram for illustrating an exemplary method for analyzing a component of the measured force by the apparatus for evaluating force control ability. Referring to FIG. 2, the magnitude and direction of the force may be represented based on the x-axis and y-axis. An arrow T represents the target force direction and the reference force magnitude. That is, the target force direction is in the y-axis direction and the reference force magnitude is indicated by the length of the arrow. For example, the user may recognize the target force direction through the arrow image displayed on the display 20 by the display unit 110 and will apply a force to the force measurement tool 30 in the target force direction. The measuring unit 120 measures the magnitude and direction of the force applied at the present to the tool based on the inclination direction, torque and moving speed of the component of the tool (for example, a stick that may be inclined in a state of being gripped by the hand).

According to an embodiment, the magnitude and direction of the force may be represented by an arrow in a three-dimensional coordinate system. In the example of FIG. 2, the direction and magnitude of the force applied by the user are indicated by an arrow R in the three-dimensional coordinate system, which may be divided into a force component $R_x$ in the x-axis direction, a force component $R_y$ in the y-axis direction and a force component $R_z$ in the z-axis direction. The processing unit 130 extracts $R_y$, which is a component of the force applied in the same direction as the target force direction, namely in the y-axis direction, among the components of the measured force, and compares the force magnitude of the component $R_y$ (that is, the length of the arrow $R_y$) with the reference force magnitude (that is, the length of the arrow T) to evaluate the force control ability of the user in the corresponding direction.

If a joint or muscle nerve is damaged due to an injury to a body part such as a hand or arm, the patient is difficult to apply a force in a desired direction through the body part (that is, it is difficult to control the force as desired). The force control ability may be appropriately evaluated by extracting only a force according to the direction in which the user wants to apply the force (namely, the target force direction) among the components of the applied force and comparing the extracted force with the reference as in the embodiment.

The evaluation result of the force control ability may be processed in various forms. For example, as shown in FIG. 2, if the target force direction is not identical to the direction of the actually applied force, a corresponding error (namely, an angle formed by the straight lines of the arrow T and the arrow R) may be converted into a score and expressed. As another example, a difference between the reference force magnitude and the actually applied force magnitude (namely, a difference in lengths between the arrow T and the arrow R) may be expressed as a score. The evaluation result of force control ability may be processed and provided to the user in an appropriate manner depending on the purpose of the evaluation or the configuration of a rehabilitation training program.

According to an embodiment, the processing unit 130 may be configured to display a result and feedback information according to the user force control ability evaluation through the display unit 120. For example, the display unit 120 may convert the evaluation result generated by the processing unit 130, namely an error of the reference value and the measured value for the direction and magnitude of the force, into a score, and display the score on the display 20. In addition, as shown in FIG. 2, if the direction of the actually measured force is biased to the right compared to the target force direction, feedback information such as "Force direction is biased to the right" or "Adjust force direction to the left" may be provided with a message or voice to help rehabilitation training of the user. If the measured force magnitude is less than the reference force magnitude, feedback information such as "Please add more force" may be provided.

According to an embodiment, the feedback information may include diagnosis information about a body part of the user with weak force control ability. The diagnosis information about the weak part may be generated based on a database in which data about damage to the body part and a resulting deterioration in body function are stored. For example, if the rotator cuff of the right shoulder is damaged, it may be difficult to push an object forward with the right hand. Thus, if the force to push the object forward with the right hand is measured to be weaker than the reference value as a result of the force measurement, diagnosis information that the rotator cuff is weak may be provided to the user.

According to an additional embodiment of the present disclosure, the apparatus for evaluating force control ability may further include a fixing unit for fixing a portion of the body of the user so that a force by body parts other than the body part subject to evaluation does not intervene. This is because the ability of the body to generate power varies according to posture. For example, when evaluating the force control ability of the right arm, the chest area may be fixed using the fixing unit so that muscles other than the right arm, such as the right pectoral muscle, do not intervene. The fixing unit may be configured to be easily attached to and detached from the body or clothing of the user, like a strap.

The display unit, the measuring unit, the processing unit, and the additional components mentioned above are distinguishably expressed for easy understanding of the function and role of the apparatus for evaluating force control ability, so the components need not be independently implemented by individual devices or programs. That is, all components may be implemented by one processor included in one computer or may be independently implemented by a plurality of computers or processors. In addition, the display unit may be interpreted in a comprehensive sense as including a display device such as a display and elements for connecting the display device to a computer, and the measuring unit may also be interpreted in a comprehensive sense as including a measuring tool and elements for connecting the measuring tool to a computer.

According to another embodiment of the present disclosure, there may also be provided an apparatus for evaluating force control ability of a prosthesis by measuring a direction and magnitude of a force applied to a measurement tool using a prosthesis worn by the user and comparing the direction and magnitude with the target force direction and the reference force magnitude. The prosthesis refers to an artificially manufactured auxiliary device that may be attached to a cut portion of a user whose upper limb is partially cut, so that the user may use some functions of the upper limb by the prosthesis. A recently developed prosthesis is being fabricated so that the user may move the prosthesis at a desired angle by using power such as electric power and gas pressure. It is very important to objectively evaluate the performance of the prosthesis (namely, the function of assisting the interaction with an object) because the cut portion is different for each user and the utilization ability of the prosthesis is also different.

Accordingly, the present disclosure provides an apparatus capable of quantitatively evaluating force control ability of the prosthesis by moving the force measurement tool in a state of wearing the prosthesis and measuring the direction and magnitude of the force accordingly. The apparatus for evaluating force control ability of a prosthesis according to an embodiment may include a display unit configured to display a target force direction, a measuring unit configured to measure a direction and magnitude of a force applied by a user through a prosthesis; and a processing unit configured to evaluate force control ability of the prosthesis by comparing the measured force direction with the target force direction and comparing the measured force magnitude with a predetermined reference force magnitude. The function and coupling relationship of the components of the apparatus are similar to the apparatus for evaluating force control ability according to the former embodiment and thus will not be described again.

Figure 3:
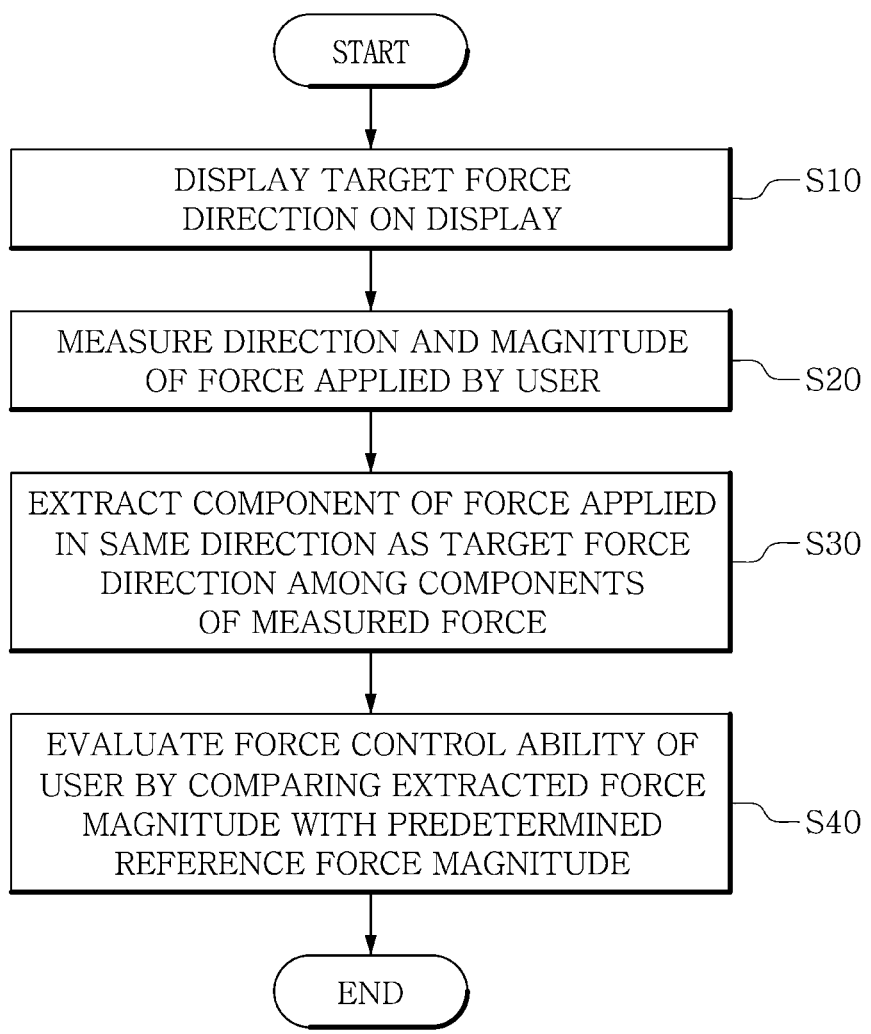
FIG. 3 is a flowchart for illustrating steps of a method for evaluating force control ability according to an embodiment.

FIG. 3 is a flowchart for illustrating steps of a method for evaluating force control ability according to an embodiment. The method for evaluating force control ability may be performed by a processor included in a computer. The steps may be implemented by one processor included in one computer or may be independently implemented by a plurality of computers or processors.

Referring to FIG. 3, first, a step of displaying a target force direction on the display is performed (S10). As shown in FIG. 1, the image D in the form of an arrow pointing a downward direction is output on the display 20 to instruct the user to apply a force in the target force direction, namely in a downward direction. The image D shown in FIG. 1 is an example, and various types of images indicating a specific direction may be used, as described above.

Subsequently, a step of measuring a direction and magnitude of the force applied by the user is performed (S20). As shown in FIG. 1, the force measurement tool 30 according to an embodiment may be manufactured to be gripped and moved in various directions by the user. The force measurement tool may include a sensor capable of detecting changes in an inclination direction, speed, and torque of the bar. The information detected by the sensor, namely information related to the direction and magnitude of the force, is converted into an electrical signal and transmitted to the processor, and the processor measures the direction and magnitude of the force applied at the present to the measurement tool based on the input signal.

Subsequently, a step of extracting a component of the force applied in the same direction as the target force direction among components of the measured force is performed (S30). As described above with reference to FIG. 2, the direction and magnitude of the force applied by the user are indicated by the arrow R, which may be divided into a force component $R_x$ in the x-axis direction, a force component $R_y$ in the y-axis direction and a force component $R_z$ in the z-axis direction. The processor extracts $R_y$, which is a component of the force applied in the same direction as the target force direction, namely in the y-axis direction, among the components of the measured force.

Subsequently, a step of evaluating the force control ability of the user is performed by comparing the magnitude of the extracted force with the predetermined reference force magnitude (S40). If a joint or muscle nerve is damaged due to an injury to a body part such as a hand or arm, the patient becomes difficult to apply a force in a desired direction through the body part, so the control ability is evaluated by comparing only the force in the same direction as the desired direction (namely, the target force direction) among the components of the applied force. The results and feedback information according to the evaluation of the force control ability of the user may be output through the display again.

The method for evaluating force control ability according to an embodiment may be implemented as an application or in the form of program instructions that may be executed through various computer components and recorded in a computer-readable recording medium. The computer-readable recording medium may include program instructions, data files, data structures, and the like alone or in combination.

Examples of the computer-readable recording medium include magnetic media such as hard disks, floppy disks and magnetic tapes, optical recording media such as CD-ROMs and DVDs, magnetic-optical media such as floptical disks, and hardware devices specially configured to store and execute program instructions such as ROM, RAM and flash memory.

If the apparatus and method for evaluating force control ability according to an embodiment of the present disclosure are used, unlike the prior art where the control ability of a user is evaluated simply according to the time taken to perform a motion, it is possible to evaluate the force control ability required to interact directly with an object by using a body part (hand, arm, shoulder, or the like) of the user. According to the embodiment, it is possible to quantitatively evaluate the force control ability of a body part interacting with the object while minimizing the intervention of other body parts that are not injured. According to the quantitative evaluation method, a body part with weak force control ability may be diagnosed objectively, thereby improving the efficiency of rehabilitation training.

According to another embodiment of the present disclosure, it is possible to quantitatively evaluate the force control ability of a prosthesis by measuring a direction and magnitude of a force applied to a measurement tool in a state where the user wears the prosthesis and comparing the direction and magnitude with a target force direction and a reference force magnitude. Even though it is impossible to quantitatively evaluate control performance of the prosthesis in the prior art, according to the present disclosure, the design and performance of the prosthesis may be supplemented by finding a weak part of the prosthesis (namely, a part where the magnitude or direction of the force is not controlled as desired).

Although the present disclosure has been described with reference to embodiments, it should be understood that the present disclosure can be modified and changed in various ways by those skilled in the art without departing from the idea and scope of the present disclosure defined in the appended claims.

What is claimed is:

1. An apparatus for evaluating force control ability, comprising:
   a display unit configured to display a target force direction to a user;
   at least one accelerometer configured to measure a direction and magnitude of a force applied by a prosthesis that is being worn by the user;
   a processor configured to evaluate the force control ability of the user by comparing the measured direction of the force with the target force direction and comparing the measured magnitude of the force with a predetermined reference force magnitude to generate an error reference value; and
   a strap configured to fix a portion of a body of the user so that a force by body parts other than the prosthesis being worn by the user does not intervene,
   wherein the processor is configured to display feedback information according to the evaluation of the force control ability of the user through the display unit,
   wherein the feedback information includes instructions for the user to modify the direction of the force applied by the user, wherein the feedback information includes diagnosis information about the user's force control ability and the identification of a weak part of a specific body part, based on data about the specific body part damage and a resulting deterioration in body function stored in a database,
   wherein the processor is configured to identify a weak part of the prosthesis by:
   extracting a component of the force applied in a same direction as the target force direction among components of the measured force and comparing a magnitude of the extracted force component with a predetermined reference force magnitude to determine where the magnitude or direction of the force is not controlled as desired, and
   wherein the processor is further configured to convert the error reference value into a score that represents an error between the target force direction and the measured force direction, and to provide the score as part of the feedback information to identify the weak part of the specific body part.

2. An apparatus for evaluating force control ability of a prosthesis being worn by a user, comprising:
   a display unit configured to display a target force direction;
   at least one accelerometer configured to measure a direction and magnitude of a force applied by the user through the prosthesis; and
   a processor configured to evaluate the force control ability of the prosthesis by comparing the measured force direction with the target force direction and comparing the measured force magnitude with a predetermined reference force magnitude to generate an error reference value; and a strap configured to fix a portion of a body of the user so that a force by body parts other than the prosthesis being worn by the user does not intervene,
   wherein the processor is configured to display feedback information according to the evaluation of the force control ability of the user through the display unit,
   wherein the feedback information includes instructions for the user to modify the direction of the force applied by the user, wherein the feedback information includes diagnosis information about the user's force control ability and the identification of a weak part of a specific body part, based on about about the specific body part damage and a resulting deterioration in body function stored in a database,
   wherein the processor is configured to identify a weak part of the prosthesis by:
   extracting a component of the force applied in a same direction as the target force direction among components of the measured force and comparing a magnitude of the extracted force component with a predetermined reference force magnitude to determine where the magnitude or direction of the force is not controlled as desired, and
   wherein the processor is further configured to convert the error reference value into a score that represents an error between the target force direction and the measured force direction, and to provide the score as part of the feedback information to identify the weak part of the specific body part.

* * * * *